US00PP11071P

United States Patent [19]

Snapp, Jr.

[11] Patent Number: Plant 11,071

[45] Date of Patent: Sep. 28, 1999

[54] APPLE TREE NAMED 'AS510'

[75] Inventor: Alfred L. Snapp, Jr., Winchester, Va.

[73] Assignee: Adams County Nursery, Inc., Aspers, Pa.

[21] Appl. No.: 08/893,478

[22] Filed: Jul. 11, 1997

[51] Int. Cl.[6] ..... A01H 5/00

[52] U.S. Cl. ..... Plt./167

[58] Field of Search ..... Plt./34.1, 167, Plt./161

*Primary Examiner*—Howard J. Locker
*Assistant Examiner*—Melissa L. Kimball
*Attorney, Agent, or Firm*—James A. Lucas

[57] ABSTRACT

A new and distinct sport of apple tree, named AS510, originated as a limb mutation on a '201 Stayman' tree. It matures earlier than 'Stayman' and develops red color ten days earlier than the parent sport. Other significant improvements over standard sports include increased color intensity, a higher percentage of red color and smaller levels of russet and scarf skin.

3 Drawing Sheets

BACKGROUND OF THE DISCLOSURE

This invention relates to Apple Trees and, more specifically, to apple trees referred to as a sport, of *Malus domestica* Borkh. 'Stayman' (unpatented).

I discovered this new and unique sport of apple tree as a limb mutation on a '201 Stayman' (unpatented) in a cultivated area near Winchester, Va. The tree of this invention produces a fruit of attractive commercial value, ripening one week before '201 Stayman'.

This new sport of apple was asexually reproduced by grafting near Biglerville, Pa. and New Paris, Pa. and such reproduction has shown this new sport to come true in three successive generation. This propagation of the new sport by grafting under standard controlled conditions clearly discloses the continued maintenance of the characteristics described herein which distinguish this new sport from the parent sport and other sports of 'Stayman'.

SUMMARY OF THE INVENTION

This new and distinctive sport of apple tree produces a solid red fruit with an attractive finish. It develops red color ten days earlier than '201 Stayman'. Color intensity and percent red color are superior to '201 Stayman' and 'Stayman'.

DESCRIPTION OF THE DRAWINGS

This new sport of apple tree is illustrated by the accompanying photographic drawings, depicting the plant by the best possible color representation using color photography.

BOTANICAL DESCRIPTION OF THE PLANT

Figure 1:
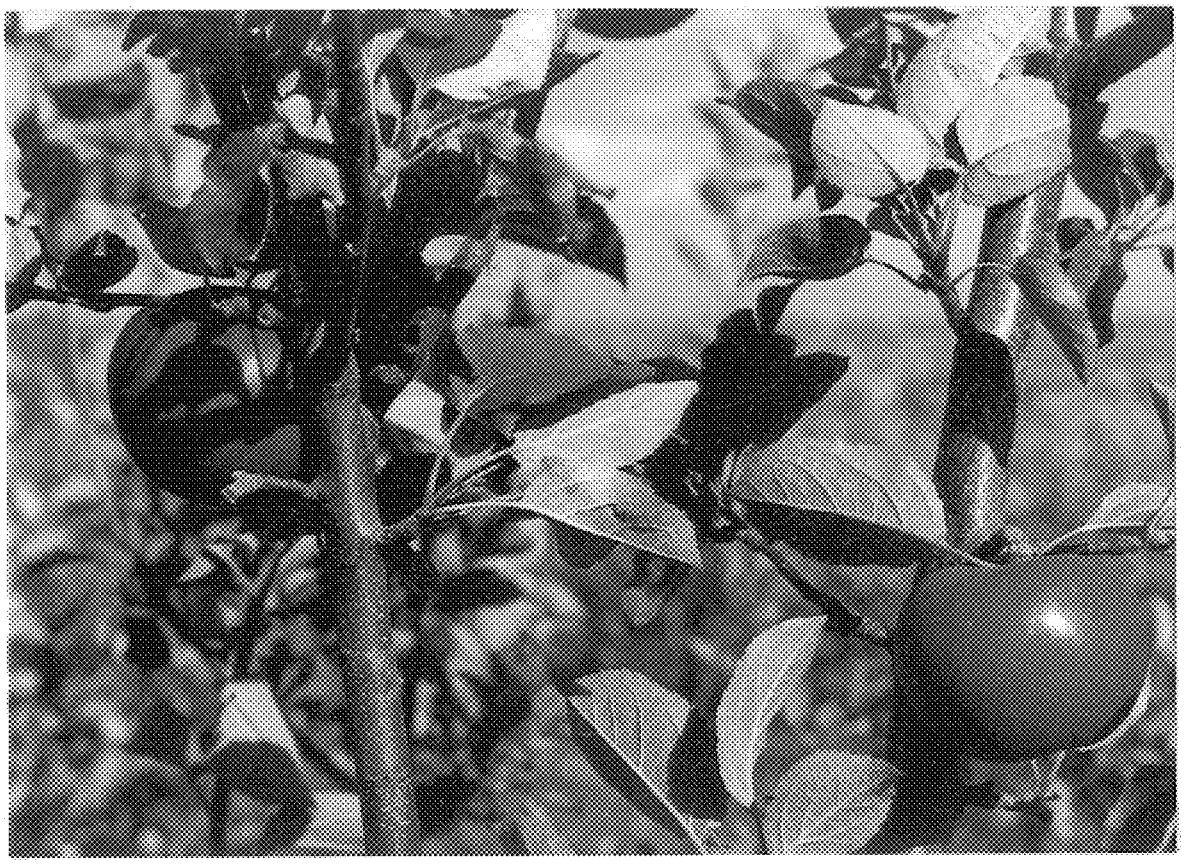
FIG. 1: Close-up of fruit on a five-year-old tree, reflecting the uniform size, shape and characteristic color.
Figure 2:
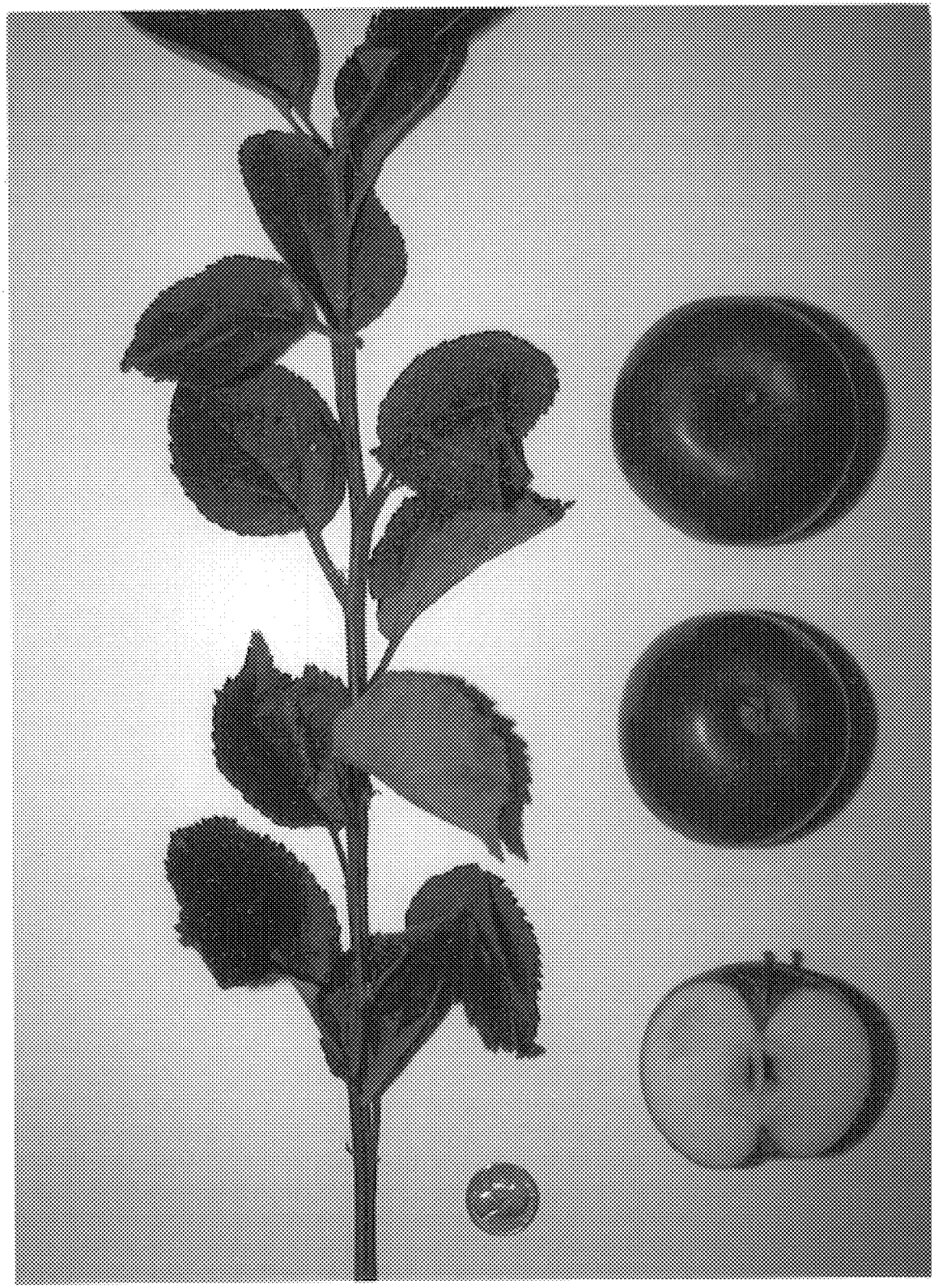
FIG. 2: Close-up of fruit and shoot characteristics showing whole fruit from calyx or stem end; a partially dissected specimen showing seed cavity and flesh color; and a terminal shoot from a five-year-old tree showing current season's growth, leaves, leaf arrangement and leaf spacing.
Figure 3:
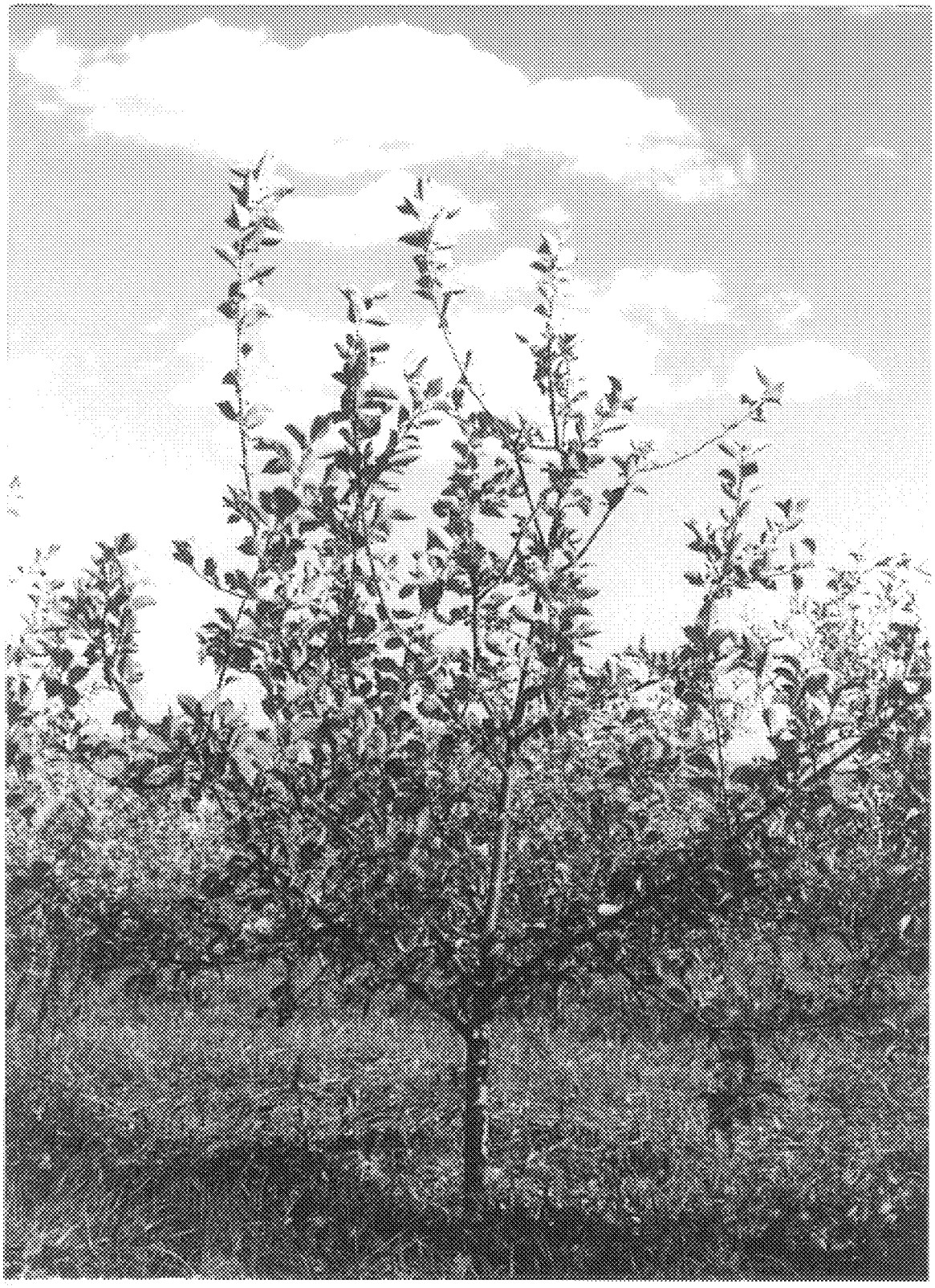
FIG. 3: Second generation, five-year-old tree, showing canopy form.

All color references below are measured against The Royal Horticultural Society (R.H.S.) Colour Chart. Colors are approximate as color depends on horticultural practices such as light level and fertilization rate, among others.

Parentage: Limb sport on a '201 Stayman' tree; asexually reproduced by bud grafting.

Tree: Tree size and productivity similar to '201 Stayman' and 'Stayman', being 11 ft. tall by 9 ft. wide and yielding 2 bushels per tree on M.7 EMLA rootstock, at five years of age, near New Paris, Pa. Large, vigorous, spreading, tall, round-topped, rapid growing, hardy, medium productive, and regular bearer.

*Trunk.*—Medium girth, medium smooth, red-gray, R.H.S 182D.

*Branches.*—Thick, smooth, little branching, red-gray, R.H.S. 182D.

*Lenticels.*—Few, large.

*Leaves.*—Length — 3¼ inches. Width — 2½ inches. Large, wide, medium length, oval, abruptly pointed, thick, smooth, dark green, R.H.S. 137B. Margins — Coarsely serrate. Petioles — Length ⅞ inches, long, thick, red-gray, R.H.S 182D.

*Flowers.*—Dates of first and full blossoms — April 28 and May 3, in New Paris, Pa. Early, similar to '201 Stayman'. Must be pollinated with another early blooming cultivar such as 'Golden Delicious' (unpatented). Size — Large. Color — White with light pink tint, R.H.S. 69D.

*Fruit.*—Maturity when described — Eating. Date — Oct. 26 ,1996. Size — Uniform, similar to '201 Stayman'. Axial diameter — 2⅞ inches. Transverse diameter — 2⅜ inches. Form — Uniform, symmetrical, regular, oblate. Cavity — Symmetrical, deep, rounded, depth ⅝ inch, breadth ⅝ inch, very lightly russeted. Stem — Slender, pubescent, length ½ inch, 0 to 2 bracts. Stem color — red gray, R.H.S. 182A. Basin — Symmetrical, shallow, smooth. Calyx — Closed, obtuse, diameter ⅝ inch, converged from base toward center. Eye — Small, partially closed. Skin — Thin, tough, smoother than '201 Stayman', glossy. Lenticels — Conspicuous, medium-sized, smaller diameter than '201 Stayman', even, circular, white, increasing numbers toward basin. Ground color — Light yellow-orange, R.H.S. 20D. Color markings — Semi-striped, bright, red-purple, 59A. Bloom — Scant. Scarf skin — Wanting, a little near cavity. Present on less than 5% of fruit surface, compared to 5–30% on '201 Stayman'. General color effect — Solid red-purple (99% of fruit surface), R.H.S. 59A. More intense than '201 Stayman'. Flesh — Juicy, white with yellowish tint, R.H.S. 158C, tinged with red in cortex near skin and vascular bundles. Texture — Firm, crisp. Flavor — Acid. Aroma — Pronounced. Eating quality — Best. Core — Median. Core lines — Clasping, green, some reddish tinge. Cross section — Indistinct. Carpellary area — Distinct, medium. Calyx tube — Glabrous, cone-shaped. Depth of tube to shoulder — ¼ inch. Entire depth — 7/16 inch. Style remnants — Present, united toward base, glabrous throughout. Stamen remnants — In one whorl, basal. Seed cells — Axile, open. Cell walls — Thin, length ½ inch, breadth 1/16 to ⅛ inch. Longitudinal section — Elliptical, acute at apex, surface smooth. Cross section — Broad. Seeds — Number perfect 10, largest number in one cell 2, length ⅜ inch, breadth 3/16 inch, form acuminate, color — brown, R.H.S. 175A.

*Uses.*—Local, dessert, culinary markets.

*Keeping quality.*—Good, 120 days in ordinary storage.

*Resistance to insects.*—Medium.

*Resistance to diseases.*—Medium.

I claim:

1. A new and distinct sport of apple tree, as illustrated and described, characterized by fruit of early maturity, attractive full red color, and excellent finish.

* * * * *